(12) United States Patent
Vastenaeken et al.

(10) Patent No.: US 6,379,044 B1
(45) Date of Patent: Apr. 30, 2002

(54) RADIOGRAPHIC IMAGE RECORDING METHOD AND APPARATUS

(75) Inventors: Guy Vastenaeken, Wespelaar; Jürgen Van Limbergen, Bonheiden, both of (BE)

(73) Assignee: AGFA-Gevaert, Mortsel (BE)

(*) Notice: Subject to any disclaimer, the term of this patent is extended or adjusted under 35 U.S.C. 154(b) by 0 days.

(21) Appl. No.: 09/707,598

(22) Filed: Nov. 7, 2000

Related U.S. Application Data

(60) Provisional application No. 60/170,884, filed on Dec. 15, 1999.

(30) Foreign Application Priority Data

Nov. 11, 1999 (EP) .............................................. 99203790

(51) Int. Cl.$^7$ ................................................. H05G 1/00
(52) U.S. Cl. ......................... 378/207; 378/116; 378/165
(58) Field of Search ............................... 378/98.7, 98.8, 378/165, 207, 116; 250/337, 327.2

(56) References Cited

U.S. PATENT DOCUMENTS

| 4,641,242 A | * | 2/1987 | Kimura | 250/337 |
| 4,960,994 A | * | 10/1990 | Mueller et al. | 250/327.2 |
| 5,264,684 A | * | 11/1993 | Weil | 250/327.2 |

FOREIGN PATENT DOCUMENTS

| EP | 0 346 530 | 12/1989 |
| EP | 0 432 119 | 6/1991 |
| EP | 0 432 722 | 6/1991 |
| EP | 0 777 406 | 6/1997 |
| EP | 99 20 3790 | 4/2000 |

\* cited by examiner

Primary Examiner—David P. Porta
Assistant Examiner—Therese Barber
(74) Attorney, Agent, or Firm—John A. Merecki; Hoffman, Warnick & D'Alessandro LLC

(57) ABSTRACT

In a radiographic image recording method and apparatus, the output of a source of radiation is adjusted taking into account the characteristics of an identified recording medium and the deviation of the actual processing conditions from expected processing conditions.

11 Claims, 1 Drawing Sheet

RADIOGRAPHIC IMAGE RECORDING METHOD AND APPARATUS

This application claims benefit of provisional application 60/170,884, filed Dec. 15, 1999.

FIELD OF THE INVENTION

The present invention relates to a method and an apparatus for recording a radiation image on a recording medium.

The invention more particularly relates to such a method and apparatus for use in the field of mammographic radiation image recording.

BACKGROUND OF THE INVENTION

In mammography a radiation image obtained through X-ray exposure of a patient's breast is commonly recorded in a dedicated mammographic image recording apparatus on a recording material such as a light-sensitive photographic film.

Such a dedicated image recording apparatus generally consists of a X-ray generator controlling the amount and the characteristics of the X-rays emitted by an X-ray source, a support for supporting the breast that it to be irradiated and a slide wherein a recording system, for example a cassette comprising a light-sensitive recording material and an intensifying screen, is positioned so that it is exposed to X-rays transmitted through the breast. The apparatus commonly also comprises an electronic signal processing unit by means of which different irradiation programs can be selected and by means of which the settings of the different parts of the apparatus are controlled and adjusted.

Mammographic images are taken when there is an instant need for diagnosis, e.g. when the patient is referred to the radiography department e.g. on request of a gynaecologist.

Apart from these occasions, mammographic images are frequently taken as a part of breast cancer screening programs.

Breast screening programs comprise the recording of a mammographic image of a person on repeated occasions, for example once a year. Part of the screening is a comparison of the mammographies taken in past years with a newly taken mammography in order to detect any changes in the breast tissue or in order to follow the evolution of suspicious elements which have been detected in the breast.

A prerequisite for optimal comparison of mammographies taken at different points of time e.g. as a part of such screening programs is that the image quality of the mammographic image is high, i.e. that a high resolution and high contrast image is obtained, and that this high quality remains constant over time. Even very small differences in the photographic characteristics of the mammographies may have an influence on the results of a comparison of mammographic images taken at different points in time, such differences may make such a comparison an unreliable basis for diagnosis.

This fact has been recognised by several international organisations among which the American College of Radiology: "Widespread mammographic screening has the potential to significantly reduce mortality from breast cancer. However, the effectiveness and success of such screening and of all mammography depends on the consistent production of high resolution, high contrast mammographic images".

Several organisations have recommended the performance of quality assurance tests and have set up detailed manuals on the requirements of these tests.

Several governments have made the performance of quality assurance tests and the quality monitoring mandatory for breast screening programs to be accepted.

There is thus a constant aim among manufacturers of recording media and among manufacturers of recording equipment to enhance the consistency and the reproducibility of the image recording. As these companies are often not the same, it may be possible that the characteristics of the recording media, and more especially the occasional changes of these characteristics, are not fully known to the equipment manufacturer and can thus not be taken into account to an adequate extent.

In a radiographic image recording apparatus and more specifically in a mammographic image recording apparatus of the kind described higher, a large number of factors have an influence on the ultimate quality of the recorded image and on the consistency of the recording throughout time.

Among these factors the most important are:

the transfer function of the X-ray source, i.e. the spectrum of irradiation as a function of the set value of mAs, kV, anode characteristics, filtration of the X-ray source, the conversion of the input X-ray spectrum into an output X-ray spectrum modulated by the object that is irradiated, in casu the patient's breast, the transfer function of the recording material, In case the recording material is a photographic material this transfer function expresses the conversion of the X-ray image into a latent image.

the transfer function expressing the conversion of the latent image into a visible image.

In case the recording material is a photographic material or a photographic material which is accompanied by an intensifying phosphor screen, this material requires chemical development of the latent image to gain a visible image. This transfer function then expresses the characteristics of the development.

Although for the ease of explanation it is assumed hereinafter that the recording medium is a photographic material or a photographic material which is accompanied by an intensifying screen, other kinds of recording systems may be envisaged.

For example a photostimulable phosphor screen might also be a suitable recording material.

It is also possible to record the radiation image by means of a direct radiographic sensor such as a sensor comprising charge coupled devices or amorphous silicon flat panel detectors or the like.

It will be clear that in case the latter kinds of recording systems are used, chemical processing and corresponding adjustments are not required.

The transfer function of the X-ray source is known to the manufacturer of X-ray image recording equipment.

When setting the radiographic recording apparatus the expected characteristics of the X-ray modulation by the object that is irradiated is taken into account through the use of a model-description which is stored in the electronic signal processing unit controlling the setting of the apparatus or through intervention of the X-ray technologist having the knowledge to do so.

The effect of other very important factors however, namely the transfer function of the recording material and the characteristics of the conversion of a latent image into a visible image (which in the case of a photographic recording material are the characteristics of the chemical processing), is generally not completely known to the manufacturer of the radiographic image recording equipment.

These effects may vary to a certain extent due to batch-to-batch changes of the recording material, day-to-day variations of the processing conditions due to temperature variations, humidity, decay of the chemical properties of the processing bath, non-uniform characteristics of the intensifying screens used with a photographic film, X-ray absorption by a cassette conveying a radiographic film or intensifying screen-radiographic film combination, etc.

To a large extent these effects are taken into account by performing a calibration of the apparatus. During this calibration characteristics of the recording material as well as characteristics of the developing process (in case the recording material is a radiographic film) are determined and the recording equipment is adjusted taking into account these characteristics.

Nowadays these calibrations are generally performed by a service technician on a regular basis. However, since this kind of intervention by a service technician is expensive, the frequency of these interventions is kept rather low. Several causes of inconsistency such as day-to-day variations of the developer conditions, batch-to-batch film variations etc. occurring in between succesive interventions of the service technician cannot be solved.

Consequentially it is possible that in between two successive interventions the image quality of the radiation images becomes inconsistent.

EP 432 722 relates to an apparatus for writing information on X-ray films. More particulary means are provided for identifying a type of film, e.g. tagged with a mark S such as a notch that has been cut in each film. An exposure correction means performs corection to determine an amount of exposure that is appropriate for a particular film type. Using the determined amount of exposure, a printer is controlled to write patient identification data on the X-ray film.

EP 432 119 discloses a method for X-ray diagnosis in particular for mammography, wherein the exposure of a film or the like is regulated to an optimal level. The radiation that has passed through an object is measured by means of an arrangement of detectors and on the basis of the result of this measurement the time of exposure is regulated.

OBJECTS OF THE INVENTION

It is an object of the present invention to provide a method and an apparatus for recording a radiation image, more specifically a mammographic image, that provides consistent image quality throughout time.

It is a further object of this invention to provide such a method and apparatus without the need for augmenting the frequency of the interventions of a service technician.

Still further objects will become apparent from the description here below.

SUMMARY OF THE INVENTION

The above mentioned objects are realised by a method having the specific features defined in claim 1.

The method of the present invention is advantageous in that a high degree of consistency is obtained between radiographic images taken at different points in time. The uniform quality is obtained without the need of frequent intervention by a service technician. The higher degree of consistency can thus be obtained at a much lower cost.

The method of the present invention comprises a first step wherein a recording medium which is actually used in the image recording apparatus is identified.

By the term 'recording medium' is meant in the context of this invention the medium itself, for example a specific photographic film, a specific photostimulable phosphor screen, an X-ray sensitive solid state sensor or the like. The term is also meant to cover combinations that together form a recording system such as a photographic film —intensifying screen combination or a cassette conveying such a combination.

Identification in the context of the present invention means determining a unique identification item that is associated with the recording medium, such as an identification number, which has a one to one relation with the recording medium that is used in the X-ray recording apparatus during the ongoing X-ray recording.

An identification item can be provided on the recording medium itself or on a wrapper or cassette conveying the recording medium.

A large variety of identification items are suitable in the context of the present invention.

In one embodiment identification consists of reading a bar code which is for example provided on a cassette conveying a radiographic film and occasionally also an intensifying screen.

In another embodiment identification consists of reading an identifier, such as an identification number from an electronic memory (e.g. an EEPROM) provided on the cassette conveying a recording medium, for example an X-ray film and (an) intensifying screen(s) or a photostimulable phosphor screen.

In still another embodiment identification can consist of entering an identifier via keyboard or via other interfacing means into the recording apparatus.

Still other alternatives are possible such as infrared identification, electromagnetic identification, optical identification, mechanical identification etc.

Next, pre-stored characteristics regarding an identified recording medium are retrieved. These characteristics are for example the type of the radiographic film, the age of the radiographic film, the batch number of the film, characteristics of a certain batch number, the type of intensifying screen, attenuation characteristics of a cassette conveying a screen-film combination, the date of production of the film, etc.

Next, the adjustments of the X-ray source are set taking into account the characteristics of the individual recording medium that is actually identified.

In this way the adjustment can be set for each individual image recording taking into account the specific properties of the recording medium that is used for that specific image recording.

In case the recording medium is a radiation sensitive film or another recording medium that needs to be subjected to processing in order to render the latent radiation image visible, it is further advantageous to take into account the deviation of the applicable processing conditions from expected processing conditions when setting the adjustments of the X-ray source. This is advantagous since processing conditions may vary with time due to chemical decay or bath exhaustion, environmental changes such as temperature changes etc. Such changes of processing conditions have an effect on the image quality of the recorded radiographic image.

In the context of the present invention the words 'actual processing conditions' are to be interpreted as the instant processing conditions applicable at the time of image recording or processing conditions applicable within a time interval between successive calibrations.

Consequentially the data regarding to processing have to be communicated to the recording apparatus so that these conditions can be taken into account when setting the adjustment of the X-ray source.

The properties of the applicable processing can for example be determined by exposing a test film under controlled exposure conditions in the radiation image recording apparatus, developing the exposed test film in the processing bath, measuring characteristic parameters such as contrast and sensitivity on the developed test film and communicating the measured values to the control electronics of the image recording apparatus.

Communication of the processing properties to the recording apparatus can be performed via an electronical connection of a measuring device and the recording apparatus.

For example an exposed and developed test wedge can be measured by means of a densitometer the output of which can be fed via a cable connection to the recording apparatus. The densitometer may be a separate apparatus or may be part of the processor.

Alternatives such as optical data transmission, infrared data transmission, radiowave transmission or manual entering via keyboard etc. are also possible.

Once the recording material has been identified and the processing conditions, if applicable, have been communicated to the recording material the source of radiation is adjusted taking into account these data and a radiation image of the object on the recording medium.

The invention further discloses an apparatus as defined in claims 7–11.

Specific features for preferred embodiments of the invention are disclosed in the dependent claims.

Further advantages and embodiments of the present invention will become apparent from the following description and drawings.

DETAILED DESCRIPTION OF THE INVENTION

Figure 1:
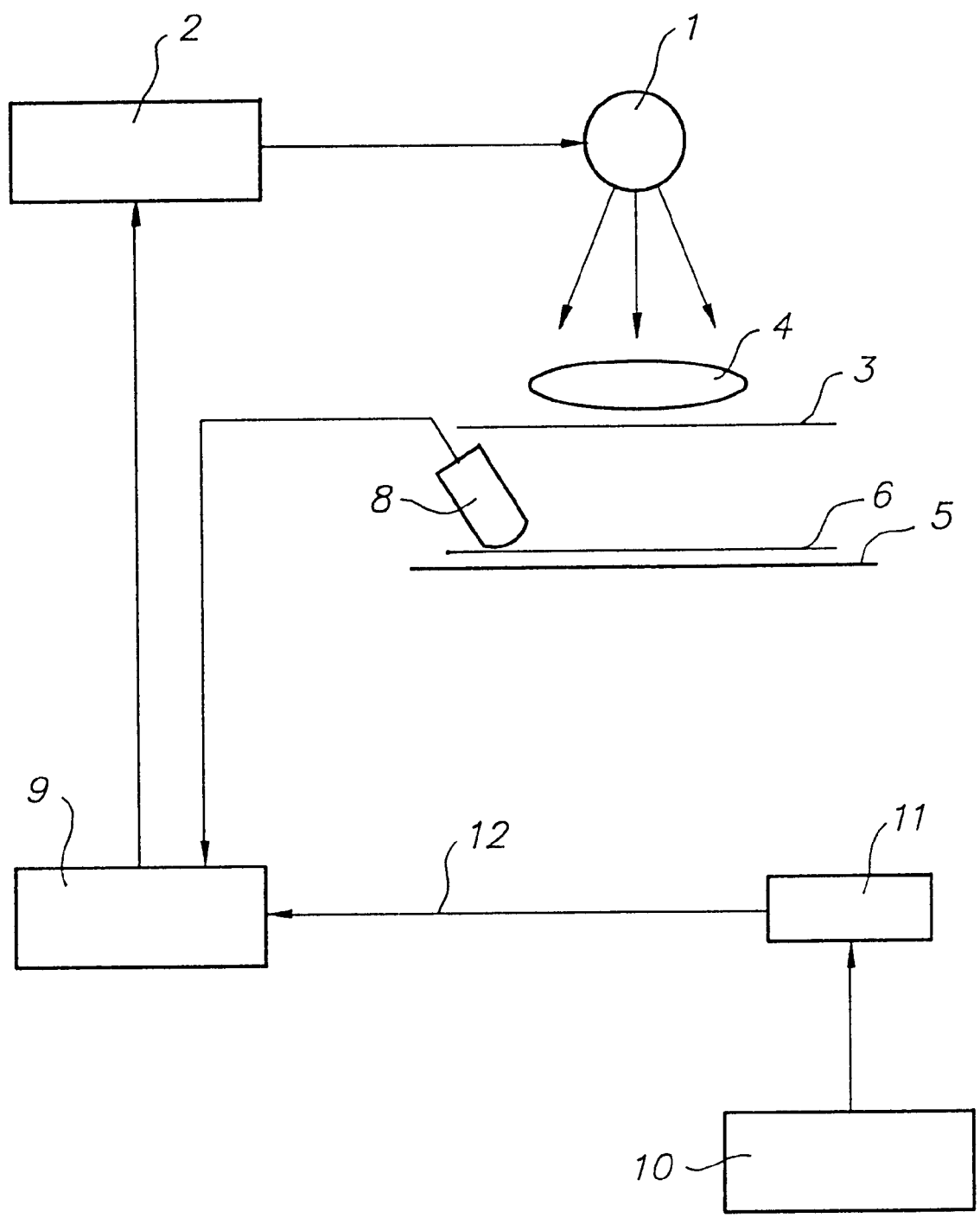
FIG. 1 shows an embodiment of an apparatus according to the present invention.

FIG. 1 schematically shows an X-ray image recording apparatus.

The apparatus comprises a source of radiation 1.

An X-ray generator 2 is connected to the X-ray source for controlling the amount and the characteristics of the X-rays emitted by an X-ray source.

The apparatus further comprises a support 3 for supporting the object 4 that is to be irradiated and a slide 5 for supporting a recording medium 6 in a position to capture X-rays modulated by the object 4.

In the illustrated embodiment the recording medium comprises a radiographic film and an intensifying screen conveyed in a cassette.

The cassette is provided with a bar code which uniquely identifies the combination of the cassette with the radiographic film and the intensifying screen actually present in the cassette.

The apparatus further comprises a bar code reader 8 which is arranged in a position for reading the bar code which is present on the cassette.

The output of bar code reader 8 is connected to electronic signal processing unit 9 which in its turn is connected to X-ray generator 2.

Electronic signal processing unit 9 comprises inter alia an electronic memory wherein characteristics of the x-ray sensitive recording media that are used in the radiation image recording apparatus are stored. The electronic memory also stores data reflecting the expected conditions of the processing bath 10 used for developing the radiographic film. These data are measured by densitometer 11.

The characteristics associated with a particular recording medium are accessible by entering an identifier which is associated with a particular recording medium.

Electronic signal processing unit 9 is programmed to run different irradiation programs which can be selected by the operator. These programs can be adapted according to the characteristics of an individual recording medium and according to the actual processing conditions. Under control of the irradiation programs the setting of the irradiation source is adjusted and controlled.

The operation of this device is as follows.

A cassette comprising a radiographic film and an intensifying screen is placed in slide 5 of the radiation image recording apparatus shown in FIG. 1. The cassette is positioned so that a bar code which in a unique way identifies the cassette which is used as well as the radiographic film and the intensifying screen actually present in the cassette, is located in the view path of bar code reader 8. The bar code is read and entered into electronic signal processing unit 9.

Likewise actual processing conditions are entered into electronic signal processing unit 9.

The actual processing conditions were obtained by determining the sensitivity and contrast of a test wedge which was irradiated under known irradiation conditions in the radiographic image recording apparatus. The data measured by densitometer 11 were communicated via a cable connection to electronic signal processing is unit 9.

Upon entering the data read out of the bar code into the electronic circuitry, retrieval of the properties of the identified cassette-film-intensifying screen combination which had been stored in advance in an electronic memory part of electronic signal processing unit 9, is started.

Also the deviation is calculated of measured processing conditions from expected processing conditions stored in advance in the electronic memory of electronic signal processing unit 9.

The X-ray source setting is determined by a selected irradiation program.

In this selected irradiation program parameters are set taking into account the actual characteristics corresponding with the identified recording medium and the deviation of measured processing conditions from expected processing conditions stored in advance in the electronic memory of electronic signal processing unit 9.

Next the object 4 to be irradiated is placed on support 3 and upon emission of X-rays by X-ray source 1 a radiation image is recorded on the recording medium which was placed in slide 5.

What is claimed is:

1. Method of recording a radiographic image of an object on a recording medium in a radiographic image recording apparatus comprising the steps of determining a unique identifier associated with said recording medium, retrieving pre-stored characteristics associated with a recording medium identified by said unique identifier, adjusting a source of radiation in correspondence with the characteristics of the identified recording medium, exposing the object to radiation emitted by said source, recording a radiation image of said object on the recording medium.

2. Method according to claim 1 wherein said recording medium is a radiographic film and wherein additionally actual film processing conditions are determined and communicated to said radiographic image recording apparatus and wherein said source of radiation is adjusted additionally taking into account the deviation of said actual film processing conditions from expected film processing conditions.

3. Method according to claim 1 wherein said identifier is a bar code.

4. Method according to claim 3 wherein said bar code is provided on a cassette conveying said recording medium.

5. Method according to claim 1 wherein said identifier is stored in an electronic memory device provided on a cassette conveying said recording medium.

6. Method according to claim 1 wherein said radiographic image is a mammography.

7. A radiographic image recording apparatus comprising a source of radiation, means for supporting an object to be irradiated, means for supporting a recording medium in the path of radiation emitted by said source, means for identifying said recording medium, electronic signal processing means wherein characteristics of recording media have been stored and by means of which characteristics of an identified recording medium can be retrieved, means for controlling the adjustment of said source of radiation taking into account the characteristics of an identified recording medium.

8. A radiographic image recording apparatus according to claim 7 wherein said recording medium is a radiographic film and, said electronic signal processing means additionally store expected processing conditions, and said electronic signal processing means are arranged for determining a deviation of actual processing conditions from expected processing conditions, means are arranged for controlling the adjustment of said source of radiation by additionally taking into account said deviation.

9. Method of recording a radiographic image of an object on a radiographic film in a radiographic image recording apparatus comprising the steps of determining actual film processing conditions, communicating actual film processing conditions to said radiographic image recording apparatus, calculating the deviation of said actual film processing conditions from expected film processing conditions, adjusting a source of radiation taking into account said deviation, exposing the object to radiation emitted by said source, recording a radiation image of said object on the recording medium.

10. A radiographic image recording apparatus comprising a source of radiation, means for supporting an object to be irradiated, means for supporting a radiographic film in the path of radiation emitted by said source, electronic signal processing means wherein expected processing conditions have been stored, means for entering actual processing conditions into electronic signal processing means, wherein electronic signal processing means are arranged for determining a deviation of actual processing conditions from expected processing conditions, means for controlling the adjustment of said source of radiation taking into account said deviation.

11. An apparatus according to claim 8 wherein said means for identifying a recording medium is a bar code reader.

* * * * *